(12) United States Patent
Zhang et al.

(10) Patent No.: US 7,723,535 B2
(45) Date of Patent: May 25, 2010

(54) ORGANOMETALLIC PRECURSOR COMPOUNDS

(75) Inventors: Delong Zhang, Grand Island, NY (US); Cynthia Hoover, Grand Island, NY (US)

(73) Assignee: Praxair Technology, Inc., Danbury, CT (US)

( * ) Notice: Subject to any disclaimer, the term of this patent is extended or adjusted under 35 U.S.C. 154(b) by 420 days.

(21) Appl. No.: 11/579,949

(22) PCT Filed: May 9, 2005

(86) PCT No.: PCT/US2005/016053

§ 371 (c)(1),
(2), (4) Date: Oct. 12, 2007

(87) PCT Pub. No.: WO2005/112101

PCT Pub. Date: Nov. 24, 2005

(65) Prior Publication Data

US 2008/0138984 A1    Jun. 12, 2008

(51) Int. Cl.
*C07F 9/00* (2006.01)
*C23C 16/00* (2006.01)
(52) U.S. Cl. .................. 556/42; 438/785; 427/255.394
(58) Field of Classification Search .................. 556/42; 427/255.394; 438/785
See application file for complete search history.

(56) References Cited

U.S. PATENT DOCUMENTS

| 6,552,209 B1 | 4/2003 | Lei et al. .................. 556/42 |
| 6,593,484 B2 | 7/2003 | Yashura et al. .................. 556/42 |

FOREIGN PATENT DOCUMENTS

JP    2003-342732    3/2003

OTHER PUBLICATIONS

Wu et al., Inorganic Chemistry, vol. 42, No. 15, pp. 4516-4518 (2003).*
Hsin-Tien Chiu et al., "Syntheses and characterization of organoimido complexes of tantalum; potential single-source precursors to tantalum nitride", *Polyhedron* vol. 17, Nos. 13-14, pp. 2187-2190, 1998.
Kyung In Choi et al., "Characteristics of ALD-TaN Thin Films Using A Novel Precursors for Copper Metallization", IITC, 2003.

* cited by examiner

*Primary Examiner*—Porfirio Nazario Gonzalez
(74) *Attorney, Agent, or Firm*—Iurie A. Schwartz

(57) ABSTRACT

This invention relates to organometallic precursor compounds represented by the formula i-PrN=Ta(NR$_1$R$_2$)$_3$ wherein R$_1$ and R$_2$ are the same or different and are alkyl having from 1 to 3 carbon atoms, provided that (i) when R$_1$ is ethyl, then R$_2$ is other than ethyl and (ii) when R$_2$ is ethyl, then R$_1$ is other than ethyl, and a method for producing a film, coating or powder from the organometallic precursor compounds.

10 Claims, No Drawings

ORGANOMETALLIC PRECURSOR COMPOUNDS

FIELD OF THE INVENTION

This invention relates to organometallic precursor compounds represented by the formula i-PrN=Ta(NR$_1$R$_2$)$_3$ wherein R$_1$ and R$_2$ are the same or different and are alkyl having from 1 to 3 carbon atoms, provided that (i) when R$_1$ is ethyl, then R$_2$ is other than ethyl and (ii) when R$_2$ is ethyl, then R$_1$ is other than ethyl, and a method for producing a film or coating from the organometallic precursor compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal-containing film on the substrate. Preferably, chemical vapor deposition precursors are volatile, heat decomposable and capable of producing uniform films under chemical vapor deposition conditions.

The semiconductor industry is currently considering the use of thin films of various metals for a variety of applications. Many organometallic complexes have been evaluated as potential precursors for the formation of these thin films. A need exists in the industry for developing new compounds and for exploring their potential as chemical vapor deposition precursors for film depositions.

Tantalum nitride (TaN) materials are being considered for a number of applications in the electronics industry for next generation devices, including copper diffusion barrier and electrodes. The industry movement from physical vapor deposition to chemical vapor deposition and atomic layer deposition processes due to the increased demand for higher uniformity and conformality in thin films has lead to a demand for suitable precursors for future semiconductor materials.

TaN film between copper interconnect and dielectrics act a barrier which prevents copper diffuses into dielectrics. Currently the TaN barrier is deposited using physical vapor deposition (PVD) technology. However, for the future generation microelectronics, where the feature size will shrink to below 65 mn, the PVD technology may not be able to deposit ultra thin conformal film to meet the challenges. Atomic layer deposition (ALD) technology is superior to PVD technology in depositing thin film. However, the challenges for ALD technology is availability of suitable precursors. ALD deposition process involves a sequence of steps. The steps include 1) adsorption of precursors on the surface of substrate; 2) purging off the precursor molecules in gas phase; 3) introducing reactants to react with precursor on the substrate surface; and 4) purging off excess reactant.

For ALD processes, the precursor should meet stringent requirements. First, the ALD precursors should be able to form a monolayer on the substrate surface either through physisorption or chemisorption under the deposition conditions. Second, the adsorbed precursor should be stable enough to prevent premature decomposition on the surface to result in high impurity. Third, the adsorbed molecule should be reactive enough to interact with reactants to leave a pure phase of the desirable material on the surface at relatively low temperature.

Prior art TaN ALD precursors have one or more of following disadvantages: 1) solid state, 2) low vapor pressure, 3) wrong phase of the deposited material, and 4) high carbon incorporation in the film. Ta(NMe$_2$)$_5$ (PDMAT) is one of the prior art candidates but it is a solid. This precursor has also a tendency to form Ta$_3$N$_5$ instead of desired TaN. Ta$_3$N$_5$ is a insulator and a undesirable phase. Another prior art TaN precursor is t-BuN=Ta(NEt$_2$)$_3$ (TBTDET), which has low vapor pressure and often results in high carbon impurity in the film.

There are three types of prior art TaN precursors, namely TaCl$_5$, Ta(NR$_2$)$_5$, R—N=Ta(NR$_2$)$_3$. TaCl$_5$ is most inexpensive among the TaN precursors. However, TaCl$_5$ is a solid and Cl incorporation in film is a serious problem. The chlorine is corrosive and will cause microelectronics device to malfunction. PDMAT does not have chloride in the composition therefore it does not have Cl incorporation problem. However, PDMAT is also a solid and has a tendency to form Ta$_3$N$_5$, which is dielectrics and is undesirable phase for barrier application. The third type of the TaN precursors is R—N=Ta(NR$_2$)$_3$ and the representative example is TBTDET. TBTDET is a volatile liquid and more favorable to form TaN phase. However, TBTDET have relatively low vapor pressure and the film deposited from TBTDET often has high carbon impurity.

In developing methods for forming thin films by chemical vapor deposition methods, a need continues to exist for chemical vapor deposition precursors that preferably are liquid at room temperature, have relatively high vapor pressure and can form uniform films. Therefore, a need continues to exist for developing new compounds and for exploring their potential as chemical vapor deposition precursors for film depositions. It would therefore be desirable in the art to provide a chemical vapor deposition precursor that is a liquid at room temperature, has a high vapor pressure and can form uniform films.

SUMMARY OF THE INVENTION

This invention pertains to chemical vapor deposition and atomic layer deposition precursors for next generation devices, specifically tantalum-containing precursors that preferably are liquid at room temperature, have relatively high vapor pressure and can form uniform films.

This invention relates in general to organometallic precursor compounds represented by the formula i-PrN=Ta(NR$_1$R$_2$)$_3$ wherein R$_1$ and R$_2$ are the same or different and are alkyl having from 1 to 3 carbon atoms, provided that (i) when R$_1$ is ethyl, then R$_2$ is other than ethyl and (ii) when R$_2$ is ethyl, then R$_1$ is other than ethyl. Typically, R$_1$ and R$_2$ are selected from methyl, ethyl, n-propyl and i-propyl.

A preferred organometallic precursor compound is i-PrN=Ta(NMeEt)$_3$ (IPTEMT). IPTEMT belongs to same class of volatile pressure as TBTDET. Both compounds contain one Ta=N bond and three Ta—N bonds. Therefore, IPTEMT has favorable inherent properties of TBTDET such as a tendency to form right tantalum nitride phase, i.e. TaN. However, ligands on IPTEMT are different from those on TBTDET. The alkyl group on imino nitrogen changes from tert-butyl in TBTDET to isopropyl in IPTEMT. The replacement of tert-butyl group by isopropyl group may increase the volatility and may also decrease the carbon incorporation. In addition, replacing diethylamido anion with ethylmethylamido anion will further increase the vapor pressure. It is expected that the vapor pressure of IPTEMT may be 10 times more volatile than TBTDET. Highly volatile precursors are desirable for CVD/ALD processes.

This invention also relates to a method for producing a film, coating or powder by decomposing an organometallic precursor compound represented by the formula i-PrN=Ta(NR$_1$R$_2$)$_3$ wherein R$_1$ and R$_2$ are the same or different and are alkyl having from 1 to 3 carbon atoms, thereby producing the film, coating or powder. Typically, the decomposing of said organometallic precursor compound is thermal, chemical, photochemical or plasma-activated.

The invention has several advantages. For example, the method of the invention is useful in generating organometallic compound precursors that have varied chemical structures and physical properties. Films generated from the organometallic compound precursors can be deposited with a short incubation time, and the films deposited from the organometallic compound precursors exhibit good smoothness.

A preferred embodiment of this invention is that the organometallic precursor compounds are liquid at room temperature and have relatively high vapor pressure. In most situations, liquids may be preferred over solids from an ease of semiconductor process integration perspective.

DETAILED DESCRIPTION OF THE INVENTION

As indicated above, this invention relates to organometallic precursor compounds represented by the formula i-PrN=Ta(NR$_1$R$_2$)$_3$ wherein R$_1$ and R$_2$ are the same or different and are alkyl having from 1 to 3 carbon atoms, provided that (i) when R$_1$ is ethyl, then R$_2$ is other than ethyl and (ii) when R$_2$ is ethyl, then R$_1$ is other than ethyl. Typically, R$_1$ and R$_2$ are selected from methyl, ethyl, n-propyl and i-propyl.

Illustrative organometallic precursor compounds of this invention include, for example, i-PrN=Ta(NMeEt)$_3$, i-PrN=Ta(NMePr)$_3$, i-PrN=Ta(NMeiPr)$_3$, and the like, wherein Me is methyl, Et is ethyl, Pr is n-propyl and iPr is i-propyl.

The organometallic precursor compounds of this invention may be prepared by conventional methods such as described in Chiu, H. T. et al, Polyhedron, 17 (1998), 2187-2190 and U.S. Pat. No. 6,552,209, the disclosures of which are incorporated herein by reference.

Examples of techniques that can be employed to characterize the organometallic compounds formed by the synthetic methods described in the above references include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

Many organometallic compound precursors described herein are liquid at room temperature and are well suited for preparing in-situ powders and coatings. For instance, a liquid organometallic compound precursor can be applied to a substrate and then heated to a temperature sufficient to decompose the precursor, thereby forming a metal-containing coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone (O$_3$), nitrous oxide (N$_2$O), water vapor, organic vapors, ammonia and others. As known in the art, the presence of an oxidizing gas, such as, for example, air, oxygen, oxygen-enriched air, O$_3$, N$_2$O or a vapor of an oxidizing organic compound, favors the formation of a metal oxide film.

As indicated above, this invention also relates in part to a process for producing a film, coating or powder. The process includes the step of decomposing at least one organometallic compound precursor, thereby producing the film, coating or powder, as further described below.

Deposition processes described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 mn to over 1 mm. The precursors described herein are particularly useful for producing thin films, e.g., films having a thickness in the range of from about 10 nm to about 100 nm. Films of tantalum nitride, for instance, can be considered for fabricating metal electrodes, in particular as n-channel metal electrodes in logic, as capacitor electrodes for DRAM applications, and as dielectric materials.

The process also is suited for preparing layered films, wherein at least two of the layers differ in phase or composition. Examples of layered film include metal-insulator-semiconductor, and metal-insulator-metal.

In an embodiment, the invention is directed to a process that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The process of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the process of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The process of the invention can be conducted to deposit a film on a substrate that has a smooth, flat surface. In an embodiment, the process is conducted to deposit a film on a substrate used in wafer manufacturing or processing. For instance, the process can be conducted to deposit a film on patterned substrates that include features such as trenches, holes or vias. Furthermore, the process of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometers thick. Films that are less than 50 nanometer thick, for instance, films that have a thickness between about 1 and about 20 nanometers, also can be produced.

Organometallic compound precursors described above also can be employed in the process of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. Nos. 6,287,965 and 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The process of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal-containing film. As described above an organometallic compound precursor can be used alone or in combination with one or more components, such as, for example, other organometallic precursors, inert carrier gases or reactive gases.

In a system that can be used in producing films by the process of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

Synthesis of i-PrN=TaCl$_3$Py$_2$

In a glove box, 7.18 grams (20 mmol) of TaCl$_5$ was placed in a 500 milliliter flask and 200 milliliters of toluene were added. Under stirring, isopropylamine (2.37 grams, 40 mmol) was added slowly using a syringe. After the mixture was stirred for 30 minutes, pyridine (6.5 milliliters) was added. The mixture was stirred for 6 hours. The resulting solid was collected by filtration and mixed with THF (100 milliliters). The mixture was stirred for 1 hour and filtered. Under vacuum, the filtrate was concentrated to obtain a solid, which was collected by filtration. Weight: 6.45 grams (12.8 mmol).

Synthesis of i-PrN=Ta(NEtMe)$_3$ (IPTEMT)

In a glove box, i-PrN=TaCl$_3$Py$_2$ (5.16 grams) was placed in a 250 milliliter flask. About 80 milliliters of hexane and 40 milliliters of THF were added into the flask. Under stirring, LiNEtMe (2.0 grams) was slowly added and the mixture was stirred overnight. All the solvent was removed to obtain a paste and 50 milliliters of hexane is added to the paste. After stirred for 2 hours, the solid was filtered off. The filtrate was transferred to a flask and concentrated to obtain a light brown liquid. The flask was brought out of glove box for vacuum distillation. Collect the distillate as the product (2.6 grams). $^1$H NMR Spectrum of IPTEMT (toluene-d$_8$): 1.15 (triplet, 18H), 1.29 (doublet, 6H), 3.43 (quintet, 12H), 4.34 ppm (septet, 1H).

The invention claimed is:

1. An organometallic precursor compound represented by the formula i-PrN=Ta(NR$_1$R$_2$)$_3$ wherein R$_1$ and R$_2$ are the same or different and are alkyl having from 1 to 3 carbon atoms, provided that (i) when R$_1$ is ethyl, then R$_2$ is other than ethyl and (ii) when R$_2$ is ethyl, then R$_1$ is other than ethyl.

2. The organometallic precursor compound of claim 1 wherein R$_1$ and R$_2$ are the same or different and are methyl, ethyl, n-propyl or i-propyl.

3. The organometallic precursor compound of claim 1 wherein R$_1$ is methyl and R$_2$ ethyl.

4. The organometallic precursor compound of claim 1 which is a liquid at room temperature.

5. A method for producing a film, coating or powder by decomposing an organometallic precursor compound of claim 1, thereby producing the film, coating or powder.

6. The method of claim 5 wherein the decomposing of said organometallic precursor compound is thermal, chemical, photochemical or plasma-activated.

7. The method of claim 5 wherein said organometallic precursor compound is vaporized and the vapor is directed into a deposition reactor housing a substrate.

8. The method of claim 7 wherein said substrate is comprised of a material selected from the group consisting of a metal, a metal silicide, a semiconductor, an insulator and a barrier material.

9. The method of claim 8 wherein said substrate is a patterned wafer.

10. The method of claim 5 wherein said film, coating or powder is produced by a gas phase deposition.

* * * * *